US009293054B2

(12) United States Patent
Bruni et al.

(10) Patent No.: US 9,293,054 B2
(45) Date of Patent: Mar. 22, 2016

(54) SYSTEMS AND METHODS TO REACT TO ENVIRONMENTAL INPUT

(71) Applicants: Sylvain Bruni, Medford, MA (US); Andy Chang, Medford, MA (US); Alan Carlin, Sunderland, MA (US); Yale Marc, Winchester, MA (US); Leah Swanson, Beavercreek, OH (US); Stephanie Pratt, Springfield, VA (US); Gilbert Mizrahi, Newton, MA (US)

(72) Inventors: Sylvain Bruni, Medford, MA (US); Andy Chang, Medford, MA (US); Alan Carlin, Sunderland, MA (US); Yale Marc, Winchester, MA (US); Leah Swanson, Beavercreek, OH (US); Stephanie Pratt, Springfield, VA (US); Gilbert Mizrahi, Newton, MA (US)

(73) Assignee: Aptima, Inc., Woburn, MA (US)

( * ) Notice: Subject to any disclaimer, the term of this patent is extended or adjusted under 35 U.S.C. 154(b) by 0 days.

(21) Appl. No.: 13/674,429

(22) Filed: Nov. 12, 2012

(65) Prior Publication Data
US 2013/0124076 A1 May 16, 2013

Related U.S. Application Data

(60) Provisional application No. 61/612,043, filed on Mar. 16, 2012, provisional application No. 61/558,487, filed on Nov. 11, 2011.

(51) Int. Cl.
G08G 5/04 (2006.01)
G08G 5/00 (2006.01)
G08G 1/16 (2006.01)
(Continued)

(52) U.S. Cl.
CPC .............. G08G 5/0095 (2013.01); G01S 13/93 (2013.01); G08G 1/16 (2013.01); G08G 5/0021 (2013.01); G08G 5/0052 (2013.01); G08G 5/0078 (2013.01); G08G 5/0091 (2013.01); G08G 5/045 (2013.01); A61B 5/18 (2013.01); B60K 28/066 (2013.01); G01S 13/9303 (2013.01)

(58) Field of Classification Search
CPC .................................................... G08G 5/0095
USPC ......... 340/436, 903, 945, 961, 963, 964, 971; 244/75.1
See application file for complete search history.

(56) References Cited

U.S. PATENT DOCUMENTS 5,111,400 A * 5/1992 Yoder ............................... 701/3
5,465,079 A * 11/1995 Bouchard et al. ............. 340/576
(Continued)

FOREIGN PATENT DOCUMENTS

WO WO2005116956 12/2005

OTHER PUBLICATIONS

Bruni, S., Chang, A., Poster session (May 2011), Trajectory Based Operations Adaptive Information Display: TBO-AID. Presented at the NASA Aviation Safety Annual Technical Meeting, St. Louis, MO, USA, May 10-12, 2011.
(Continued)

Primary Examiner — Thomas Tarcza
Assistant Examiner — Tyler J Lee
(74) Attorney, Agent, or Firm — John J Brooks III

(57) ABSTRACT

Computer implemented systems and methods of communicating a system reaction to environmental input comprising receiving environmental input, determining a hazard state and a user state from the environmental input, determining a system reaction from the hazard state and the user state and communicating the system reaction to a user interface. In some embodiments, the system reaction comprises a system reaction level and in some embodiments the system reaction level corresponds to a stage of automation. In some embodiments, the user interface is a multimodal interface and in some embodiments the user interface is a haptic interface.

20 Claims, 12 Drawing Sheets

(51) Int. Cl.
  *G01S 13/93* (2006.01)
  *A61B 5/18* (2006.01)
  *B60K 28/06* (2006.01)

(56) References Cited

U.S. PATENT DOCUMENTS

| | | | | |
|---|---|---|---|---|
| 6,060,989 | A * | 5/2000 | Gehlot | 340/576 |
| 6,906,619 | B2 * | 6/2005 | Williams et al. | 340/425.5 |
| 7,081,834 | B2 * | 7/2006 | Ruokangas et al. | 340/945 |
| 7,124,027 | B1 * | 10/2006 | Ernst et al. | 701/301 |
| 7,245,231 | B2 * | 7/2007 | Kiefer et al. | 340/903 |
| 7,302,339 | B2 * | 11/2007 | Gray | 701/36 |
| 7,383,131 | B1 * | 6/2008 | Wey et al. | 702/4 |
| 7,516,011 | B1 * | 4/2009 | Kabel et al. | 701/415 |
| 7,609,150 | B2 * | 10/2009 | Wheatley et al. | 340/436 |
| 7,917,255 | B1 * | 3/2011 | Finley | 701/9 |
| 7,932,853 | B1 * | 4/2011 | Woodell et al. | 342/26 B |
| 7,974,748 | B2 * | 7/2011 | Goerick et al. | 701/28 |
| 8,160,772 | B2 * | 4/2012 | Ito et al. | 701/36 |
| 8,384,534 | B2 * | 2/2013 | James et al. | 340/439 |
| 2002/0120374 | A1 * | 8/2002 | Douros et al. | 701/29 |
| 2003/0222795 | A1 * | 12/2003 | Holforty et al. | 340/968 |
| 2004/0049344 | A1 | 3/2004 | Simon et al. | |
| 2007/0244606 | A1 * | 10/2007 | Zhang et al. | 701/1 |
| 2008/0291032 | A1 * | 11/2008 | Prokhorov et al. | 340/576 |
| 2010/0228482 | A1 | 9/2010 | Yonak | |
| 2011/0071750 | A1 * | 3/2011 | Giovino et al. | 701/120 |

OTHER PUBLICATIONS

Saffell, T.N., Alexander, A.L., Carlin, A., Chang, A.C. and Schurr, N., Poster (2011), An integrated alerting and notification system utilizing stages of automation and uncertainty Visualization. Proceedings of the International Symposium of Aviation Psychology, Dayton, OH, USA, Wright State University, May 5, 2011.

Carlin, A., Alexander, A.L. and Schurr, N., Modeling pilot state in next generation aircraft alert systems. Presented at the MODSIM World 2010 Conference & Expo, Oct. 15, 2010, VA, USA.

Alexander, A., Saffell, T.N., Alaverdi, O., Carlin, A.S., Chang, A., Durkee, K., Falster, S.M., Geiselmen, E., Latorella, K. Wickens, C.D. and Schurr, N., Alerting and reasoning management system. NASA, Oct. 2010, VA, USA.

Carlin, A., Schurr, H. and Marecki, J., Alarms: Alerting and Reasoning Management System for Next Generation Aircraft Hazards. Proceedings of the 26th Conference on Uncertainty in Artificial Intelligence (UAI 2010). P. Grünwald and P. Spirtes (Editors). AUAI Press, Jul. 11, 2010, CA, USA.

Raja Parasuraman, Thomas B. Sheridan, Fellow, IEEE, and Christopher D. Wickens. A Model for Types and Levels of Human Interaction with Automation, IEEE Transactions on Systems, Man, and Cybernetics—Part A: Systems and Humans, vol. 30, No. 3, May 2000, New York, USA.

Susan S. Kirschenbaum and James E. Arruda, Effects of Graphic and Verbal Probability Information on Command Decision Making, Human Factors: The Journal of the Human Factors and Ergonomics Society 1994 36:406, USA, Sep. 1, 1994, CA, USA.

Nathan Schurr, Janusz Marecki and Milind Tambe, RIAACT: A robust approach to adjustable autonomy for humanmultiagent teams (Short Paper), Proc. of 7th Int. Conf. on Autonomous Agents and Multiagent Systems (AAMAS 2008), Padgham, Parkes, Müller and Parsons (eds.), May 12-16, 2008, Estoril, Portugal.

Saffell, T.N., Alexander, A.L., Carlin, A., Chang, A.C. and Schurr, N., Proceedings Paper (2011), An integrated alerting and notification system utilizing stages of automation and uncertainty Visualization. Proceedings of the International Symposium of Aviation Psychology, Dayton, OH: Wright State University, May 5, 2011, Ohio, USA.

* cited by examiner

Sensor Signals →

Potential Hazards →

623

| Tools/Technology/Systems | Sub-Systems | System Failure | System Performance Compromised | Loss of Separation | Adverse Weather Encounter | Altitude Deviation |
|---|---|---|---|---|---|---|
| Electrical (3.1.11) | | (C) | ■ | | | |
| Hydraulic (3.1.15) | | (C) | (C) | | | |
| Fuel (3.1.14) | | (C) | (C) | | | |
| Landing Gear (3.1.17) | | ■ | (C) | | | |
| Air Conditioning/Pressurization (3.1.21/22) | | ■ | (C) | | | |
| Ice Protection (3.1.16) | | | | | (C) | |
| Fire Protection (3.1.12) | | (C) | (C) | | | |
| Enhanced Ground Proximity Warning (EGPWS) (3.1.20) | | (A) | (A) | | ■ | |
| Navigation Radio (Nav Radio) | | | | | | |
| | Enroute (3.1.1) | (A) | (A) | | | |
| | Approach (3.1.1) | (A) | (A) | | | (A) |
| Flight Management System (FMS) | | | | | | |
| | RNAV (3.1.18) | (A) | (A) | | | |

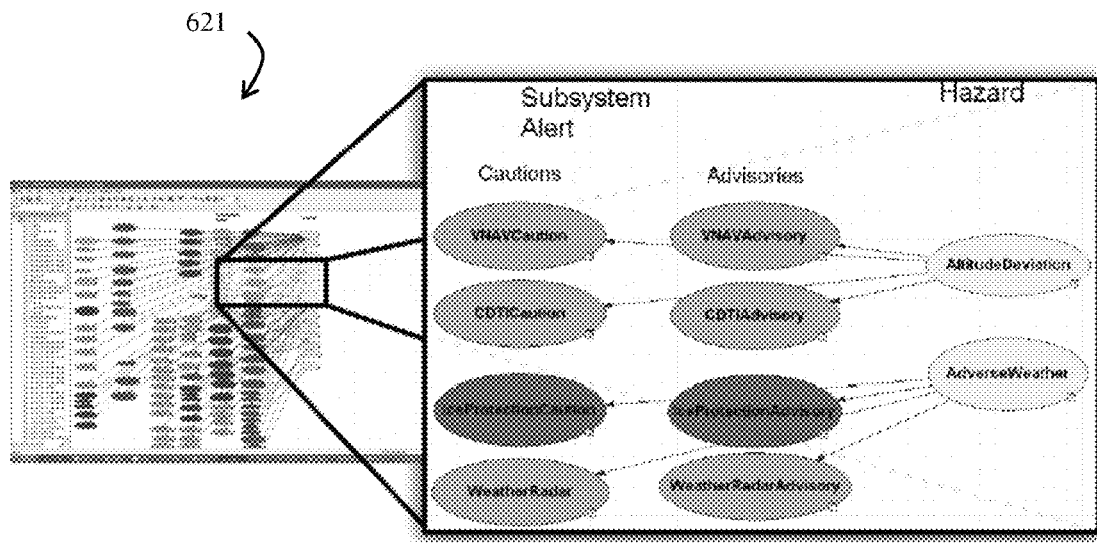

FIG. 6B

Alert / Stage Mapping

ALERT LEVELS*
- Advisory - Safe or normal condition that imparts information for routine action purposes.
- Caution - Condition requiring immediate attention but not immediate action ("timely manner").
- Warning - Hazardous condition requiring immediate action (10 to 15 seconds).
- Directive - Hazardous condition requiring instant action (<10 seconds).

INFORMATION PROCESSING STAGES
- Information Acquisition: Presence of new information
- Information Analysis: Integrated information (relative to ownship) to give information context
- Decision: Pilot chooses one of many route alternatives
- Action execution: Pilot executes route chosen by automation

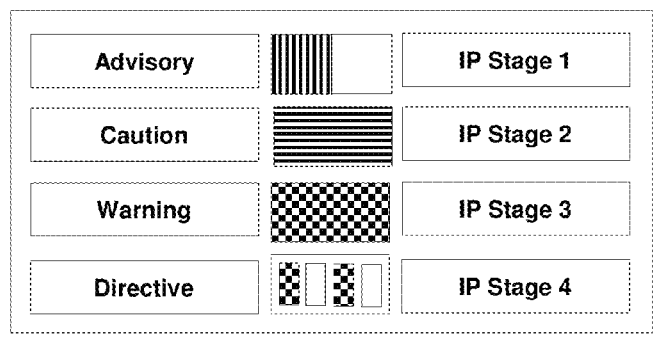

FIG. 8A

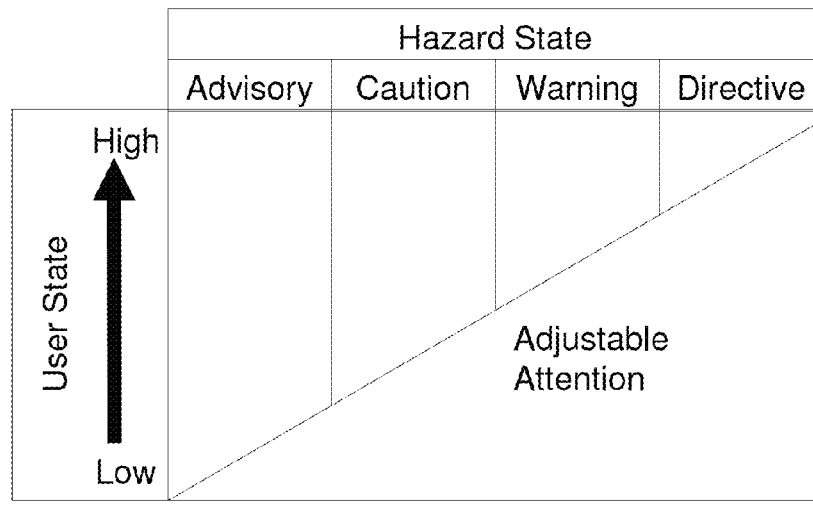

FIG. 8B

|  | Information Acquisition | Information Analysis | Decision | Action Execution |
|---|---|---|---|---|
| Directive |  |  |  | High-pitched and quick double tone as a cue to upcoming verbal command (e.g., instructions on how to reroute) & Double vibration that correlates with the auditory double tone cue |
| Warning |  |  | High-pitched and quick double tone as a cue to upcoming verbal command (e.g., "select new route") & Double vibration that correlates with the auditory double tone cue |  |
| Caution |  | Double tone to indicate presence of integrated and processed information. Double vibration (e.g., alert in pocket) to supplement the double tone |  |  |
| Advisory | Single tone to indicate presence of new information (aircraft or weather) |  |  |  |

FIG. 8C

SYSTEMS AND METHODS TO REACT TO ENVIRONMENTAL INPUT

CROSS-REFERENCE TO RELATED APPLICATIONS

This application claims the benefit of U.S. Pat. App. No. 61/558,487, filed on Nov. 11, 2012, entitled "ADAPTIVE FLIGHT DECK DISPLAY FOR TRAJECTORY-BASED OPERATIONS" and U.S. Pat. App. No. 61/612,043, filed on Mar. 16, 2012 entitled "SYSTEMS AND METHODS TO REACT TO ENVIRONMENTAL INPUT", the entire contents of both are incorporated herein by reference.

STATEMENT REGARDING FEDERALLY SPONSORED RESEARCH OR DEVELOPMENT

This invention was made with Government support under Contract Nos. NNX11CG58P and NNL08AA20B awarded by the National Aeronautics and Space Administration. The Government has certain rights in the invention.

REFERENCE TO SEQUENCE LISTING, A TABLE, OR A COMPUTER PROGRAM LISTING COMPACT DISC APPENDIX

Not Applicable

BACKGROUND OF THE INVENTION

1. Field of the Invention

Embodiments of this invention relate to the determination of a response to environmental inputs. In one particular embodiment, the systems and methods determine one or more states from environmental inputs and automatically provide an output responding to that input.

2. Description of the Prior Art

The objectives of Next Generation Air Transportation System (NextGen) revolve around increasing the safety and efficiency of air traffic, including more precise tracking and prediction of aircraft movement, as well as expanding the maximum number of aircraft potentially in flight at a given time. The vision of NextGen is one in which pilots will be responsible for following 4-dimensional (4D) trajectories while maintaining separation from other aircraft and weather. However, there is currently a lack of effective flight deck displays that support pilots who will be faced with the challenge of making more complex, strategic decisions than are required in current-day operations. In fact, the NextGen Integrated Work Plan includes an Operational Improvement for delegated responsibility for separation that specifically calls for improved displays to provide detailed traffic situation awareness to the flight deck. Pilots will also be required to contend with different data sources (e.g., data communications or DataComm, Automatic Dependant Surveillance Broadcast or ADS-B) than are currently used, and will need to integrate additional sources of information, particularly weather data, into trajectory planning and conflict avoidance.

Two key challenges to effective display design include information certainty and multimodal considerations. With respect to information certainty, uncertainty visualization is critical to TBO given the unique information needs and situation awareness requirements associated with conducting 4D operations (e.g., self-separation and self-management for deconfliction) in a dynamic and uncertain environment. With respect to multimodal considerations, research in cognition and neuroscience has produced substantial evidence that humans can enhance their information processing capabilities through the use of multiple modalities (e.g., Baddeley, 1992; Just, Carpenter, & Miyake, 2003; Wickens, 1980, 1984). In the auditory-visual context, this phenomenon may be partially explained by the fact that auditory information can be perceived without re-directing visual attention (Baldwin, 2002). Current flight decks are not equipped with technologies that dynamically adjust the mode of communication based upon this situational context. Technologies that can adapt information presentation in this manner will improve the effectiveness of joint human-automation systems in aviation. This notion of display adaptation is critical to developing a situationally-aware solution that considers contextual information to maximize system performance and minimize information processing bottlenecks by displaying the right information at the right time in the right format.

Current-day operations rely on Air Traffic Control to direct aircraft for separation from other aircraft and weather. However, in NextGen Operations, this responsibility will be delegated to the pilot of individual aircraft. As described by the Joint Planning and Development Office, trajectory-based operations (TBO) will dynamically adjust entire flows of aircraft or individual trajectories to take advantage of airspace opportunities and avoid constraints associated with weather and other aircraft that are not equipped for TBO. This type of trajectory-based control is very different from the clearance-based control of today, and will place additional responsibilities on pilots for maintaining safe and efficient operations. Displays that portray these opportunities and constraints to the flight crew to effectively convey information and its associated reliability to aid in optimized decision-making do not currently exist. Novel displays enable enhanced spatial awareness for flight crews, particularly with respect to separation from other aircraft and avoiding weather hazards. Novel display concepts will also aid in ensuring effective collaborative performance of the human-system team as the reliance on automation continues to increase.

Traditional approaches to uncertainty visualization generally represent uncertainty by providing additional data or manipulating the display of existing information. While uncertainty can be displayed as additional data elements, one pervasive concern with this design approach is the presentation of too much data, which can overload a pilot who is tasked with monitoring traditional displays and the visual scene out the window. Uncertainty can also be represented by altering the physical appearance of existing data through the use of different colors, by using gradation or texture, or by altering the shape or orientation of information icons or glyphs (e.g., Andre & Cutler, 1998; Kirschenbaum & Aruda, 1994; MacEachren, 1992).

Current operational flight decks often present multimodal information concept at a basic level—for example, the Traffic Collision Avoidance System (TCAS) is designed with auditory cues that permit pilots to visually monitor instruments simultaneously. However, in many cases the optimal modality is dependent upon the situation, including the tasks being performed, the personal attributes of the pilot, or the likelihood of hazards in the surrounding environment. Current flight decks are not equipped with technologies that dynamically adjust the mode of communication based upon this situational context.

BRIEF SUMMARY OF THE INVENTION

The following summary is included only to introduce some concepts discussed in the Detailed Description below. This summary is not comprehensive and is not intended to delineate the scope of protectable subject matter, which is set forth by the claims presented at the end.

In one example embodiment, a computer implemented method of determining a system reaction to environmental input is provided, the method comprising receiving environmental input, determining a hazard state and a user state from the environmental input, determining a system reaction from the hazard state and the user state and receiving the system reaction to a user interface. In some embodiments, the system reaction comprises a system reaction level and in some embodiments the system reaction level corresponds to a stage of automation. In some embodiments, the system reaction comprises a salience component and an intrusiveness component. In some embodiments, the user interface is a multi-modal interface and in some embodiments the user interface is a haptic interface.

In one example embodiment, a computer implemented method of determining a system reaction to environmental input is provided, the method comprising receiving a first environmental input and a second environmental input, determining a hazard state from the first environmental input, determining a user state from the second environmental input, determining a system reaction from the hazard state and the user state and communicating the system reaction to a user interface. In some embodiments, determining the user state from the second environmental input comprises automatically correlating the second environmental input to the user state utilizing a predictive index. In some embodiments, determining the user state from the second environmental input comprises automatically correlating the second environmental input to at least one user measure and correlating the at least one user measure to at least one user state utilizing a predictive index. In some embodiments, correlating the at least one user measure to the at least one user state utilizing the predictive index comprises correlating a first user measure to a first user factor to create a first user factor measure, correlating a second user measure to a second user factor to create a second user factor measure, weighing the first factor measure and second factor measure to create a weighted first user factor measure and weighted second user factor measure and determining the user state from the weighted first user factor measure and the weighted second user factor measure. In some embodiments, the hazard state is determined by a Bayesian Network and in some embodiment, the Bayesian Network outputs the hazard state as an estimate of a probability and a severity of at least one hazard. In some embodiments, determining the system reaction from the hazard state and the user state comprises determining the system reaction from the hazard state the user state and an automation reaction. In some embodiments, the automation reaction is determined by a rules-and-constraint-based algorithm and in some embodiments, the automation reaction is further determined by considering an automation effectiveness component and a user effectiveness component. In some embodiments, determining the user state from the second environmental input comprises automatically correlating the second environmental input to the user state utilizing a predictive index. In some embodiments, the system reaction further comprises a system reaction level and in some embodiments, the system reaction level comprises a salience component and an intrusiveness component.

In one example embodiment, a computer implemented method of communicating a system reaction to environmental input is provided, the method comprising receiving an environmental input, determining a hazard state from the environmental input, determining a system reaction from the hazard state, the system reaction comprising a temporal plan and communicating the system reaction to a user interface. In some embodiments, determining the system reaction from the hazard state comprises determining the temporal plan from the hazard state and a user state. In some embodiments, the user state is determined from the environmental input. In some embodiments, the user state is determined by correlating the environmental input to the user state utilizing a predictive index and the hazard state is determined by estimating the hazard state with a State Estimation Bayesian Network. In some embodiments, determining a temporal plan from the hazard state comprises determining a temporal plan from the hazard state, a user state and an automation reaction. In some embodiments, the system reaction further comprises a system reaction level. In some embodiments, the user interface is a multi-modal user interface. In some embodiments, the user interface is an intrusive user interface or a haptic interface. In some embodiments, the user interface is a multi-modal user interface having a plurality of levels of alerts, the system reaction further comprises a system reaction level and the level of alert corresponds to the system reaction level. In some embodiments, the temporal plan comprises a first incremental instruction and a second incremental instruction. In some embodiments, determining a temporal plan comprises determining a first incremental instruction and a second incremental instruction from a Time-Dependent Markov Decision Process (TMDP).

In one example embodiment, a method of determining a system reaction to environmental input is provided, the method comprising receiving an environmental input, determining a hazard state from the environmental input and determining a system reaction from the hazard state. In some embodiments, the step of determining the system reaction further comprises determining a temporal plan from the hazard state. In some embodiments, the step of determining the system reaction further comprises determining an automation system reaction. In some embodiments, the step of the step of determining the system reaction further comprises determining an alarm reaction. In some embodiments, the methods further comprise determining a user state and the step of determining the system reaction further comprises determining a temporal plan from the hazard state and the user state. In some embodiments, the hazard state is estimated with a Bayesian network, the user state is estimated through a predictive index correlating the environmental input to a user state and the temporal plan is determined through a TMDP.

In one example embodiment, a system for determining a system reaction to environmental input is provided, the system comprising an input module for receiving an environmental input, a hazard state estimation model for determining a hazard state from the environmental input and a planning model for determining a system reaction from the hazard state.

In one example embodiment, a system for communicating a system reaction to environmental input is provided, the system comprising a user interface configured to receive a system reaction and the user interface configured to communicate the system reaction.

In one example embodiment, a computer program product for determining a system reaction to environmental input is provided, the computer program product comprising a computer readable medium having a computer readable program code embodied therein, said computer readable program code configured to be executed to implement a method for determining a system reaction to environmental input, said method comprising receiving an environmental input, determining a hazard state from the environmental input, determining a temporal plan from the hazard state, determine a system reaction from the temporal plan and communicating the system reaction to a user interface.

In one example embodiment, the systems and methods to react to environmental input are used with Next Generation Air Transportation System (NextGen). The embodiment anticipates the situation that the responsibilities of aircraft pilots and the density of air traffic within the airspace are both expected to dramatically increase within the defined concept of operations for NextGen. As a result, the sheer number of potential hazards and relevant information that must be perceived and processed by the pilot will grow exponentially. An Integrated Alerting and Notification (IAN) system may continuously monitor multiple sources of interdependent information. The ALerting And Reasoning Management System (ALARMS) consists of a rigorously-tested user-centered model to drive cognitive functions and a dedicated display to portray these recommendations to the pilot. In this embodiment, ALARMS provides: information acquisition support through cognitive work analysis (CWA) functions to capture the pilot's attention and notify the presence of the hazard; enhance information integration and inference through tools to support the pilot in assessing the hazard situation relative to ownship safety; and, when appropriate, provide decision support, recommending trajectory or speed changes to the pilot to divert around or avoid safety-critical hazards.

BRIEF DESCRIPTION OF THE SEVERAL VIEWS OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 6A is a diagram of one example embodiment of a hazard matrix;

FIG. 6B is an illustration of one example embodiment of a Bayesian Network utilizing a hazard matrix;

FIGS. 8A-8C are diagrams illustrating an example of the mapping of states and alert levels to information processing states;

DETAILED DESCRIPTION OF THE INVENTION

Systems and methods to react to environmental input will now be described in detail with reference to the accompanying drawings. It will be appreciated that, while some of the following description focus on a system that provides alarm reactions for pilots, the systems and methods disclosed herein have wide applicability. For example, the environmental system reaction systems and methods described herein may be readily employed with vehicle operators such as car drivers, financial portfolio management, facility management, automated manufacturing processes or any other ongoing process that is influenced by or should react to changing user and environmental states. Notwithstanding the specific example embodiments set forth below, all such variations and modifications that would be envisioned by one of ordinary skill in the art are intended to fall within the scope of this disclosure.

Figure 1:
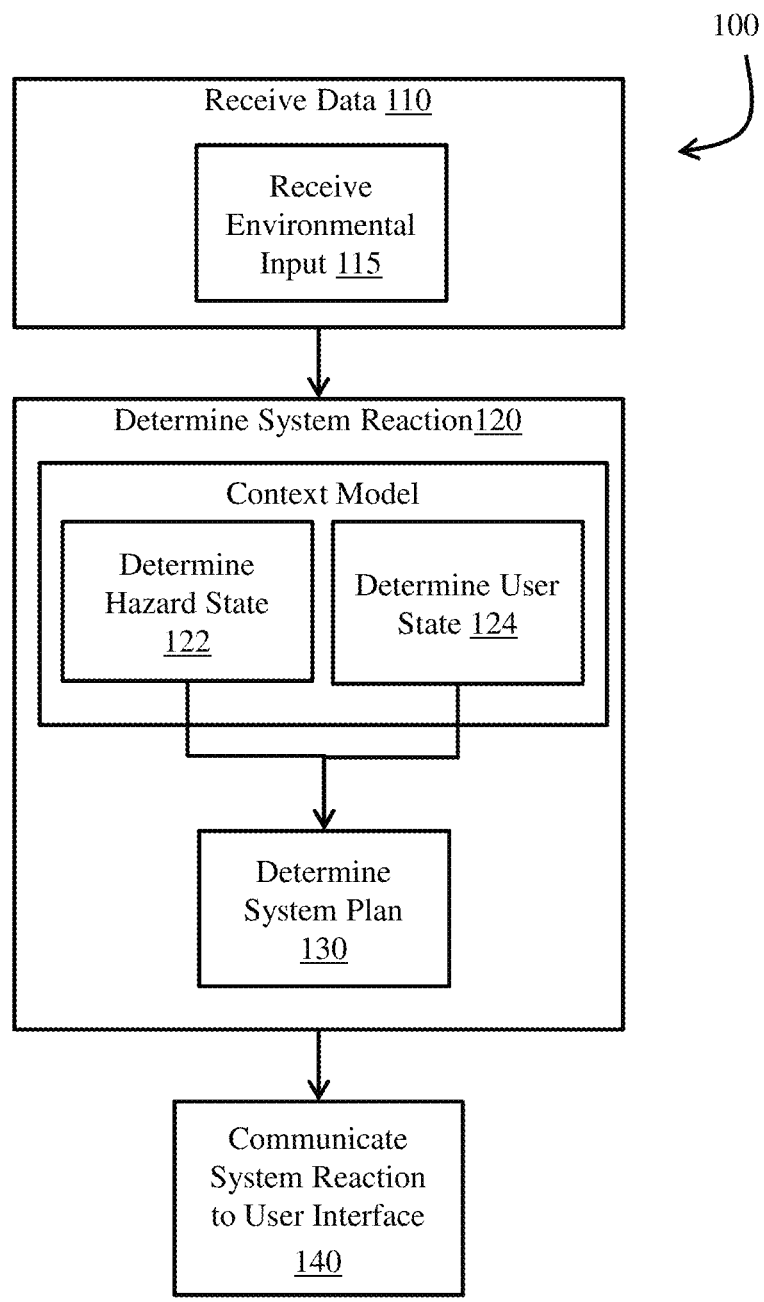
FIG. 1 is a process diagram of one example embodiment of a method to react to environmental input.

In one example illustrative embodiment, as shown in FIG. 1, a computer implemented method 100 of reacting to an environmental input comprises receiving an environmental input at 115, determining a hazard state at 122 from the first environmental input, determining a user state at 124 from the second environmental input, determining a system plan at 130 from the hazard state and the user state, determining the system reaction at 120 from the system plan and communicating the system reaction to a user interface at 140.

As used throughout this description, a system reaction may be any type of alarm, alert, information, graphic display, command, multi-step plans or any means of providing information to a user or another component of the system. A system reaction may also include a representation of the system reaction or an instruction for a system component, such as a user interface or an automation system, to provide the system reaction.

Data is received at 110 by any method of collecting and receiving data representing the environment or the user. For example, receiving environmental data may include receiving data such as sensor data (or simulated sensor data) that exists in the environment, such as information about aircraft status, local traffic, weather, and the pilot's physiology. In this embodiment, environmental input received at 115 comprises the data to be used to determine the hazard state at 122 and/or the user state at 124. The environmental input may be provided by sensors, user input, predetermined input or any other system input that may help determine the hazard and/or user state.

The hazard state is an estimation of the probability and/or severity of hazards related to the environmental inputs provided. Having a relationship between hazard states and environmental inputs, allows the hazard states to be estimated from the environmental input at 122. The hazard state is determined at 122 by a context model which analyzes the hazard state, or environmental conditions that may cause potential safety threats, to define the probability of a hazard. The context model for determining the hazard state, a hazard state estimation model, uses information about sensor alerts and hazards to correlate the sensor environmental input data into measures, in this instance hazard measures and then uses probabilistic reasoning to estimate the true state of existing hazards from the hazard measures. For example, a Bayesian Network may be constructed and used to estimate the hazard state where the input to the Bayesian Network can be the environmental inputs received from sensor systems and the output is an estimate of the probability and severity estimate of hazards reflected by the inputs.

Figure 2A:
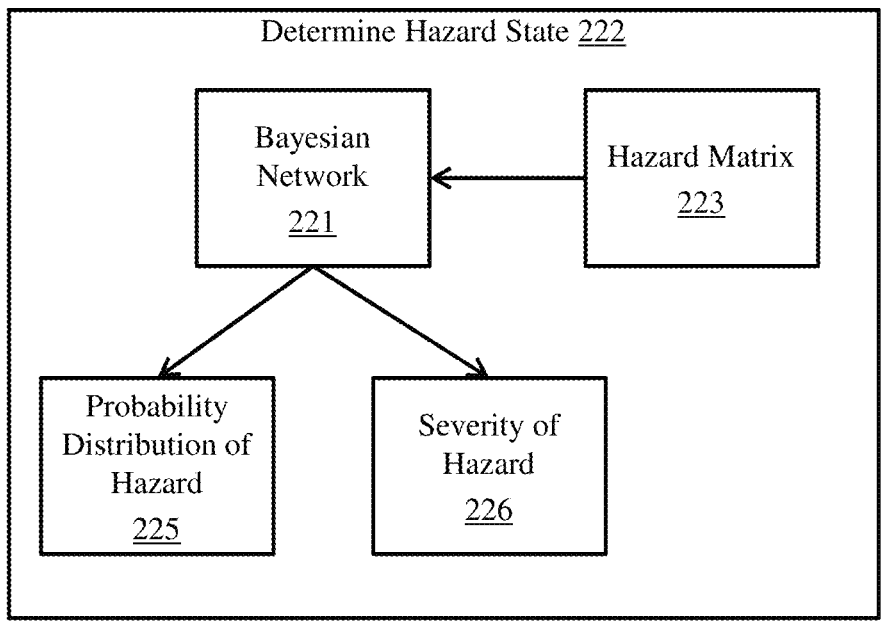
FIG. 2A is a process diagram of one example embodiment of a method of determining a hazard state.

An illustration of one embodiment of determining the hazard state is shown in FIG. 2A where the hazard state is determined at 222 through the use of a Bayesian Network 221 that exploits a hazard matrix 223. The hazard matrix 223 is a set of relationships linking potential hazards during operations and signals provided to users for the purpose of alerting them to these hazards. The hazard matrix 223 may be any method of relating variables to each other such as a table relating a type of hazard to an environmental input or sensor and a severity level of the hazard. These relationships may be gained through tools such as CWA. The data from the hazard matrix 223, populated with current and future technologies and/or sensors, may form the basis of the Bayesian Network 221, which takes in the alerts issued by the sensor systems. The Bayesian Network 221 weighs these inputs and associates them with the probability of hazards from the inputs. Using a model of the system's environment, the Bayesian Network 221 outputs a probability distribution of the various hazards. The result of these steps may be an estimate of the probability, defined as a probability distribution of the hazard 225, and a severity of the hazards 226 reflected by the sensor input.

Referring back to FIG. 1, with the hazard state estimated at 122, a system plan is determined at 130 which reflects one or more plans from the hazard state determined. The system plans may comprise any type of system reaction to the hazard state such as a single reaction, a single plan or multiple plans. These system plans are used to determine the system reaction at 120. The system plans may be analyzed to determine which plan, such as the optimum plan or the most probable plan, should be used to determine the system reaction. The system reaction may be any reaction to the estimated hazard state such as an alarm reaction to provide an alarm to the user interface and the system reaction may also be a temporal, or time-dependent, plan having a plurality of steps or incremental instructions to address the input such as a plurality of incremental points against which a policy is applied to define the system reaction at each of these incremental points. The system reaction may comprise more than one system reaction and may include a system reaction level.

Figure 3:
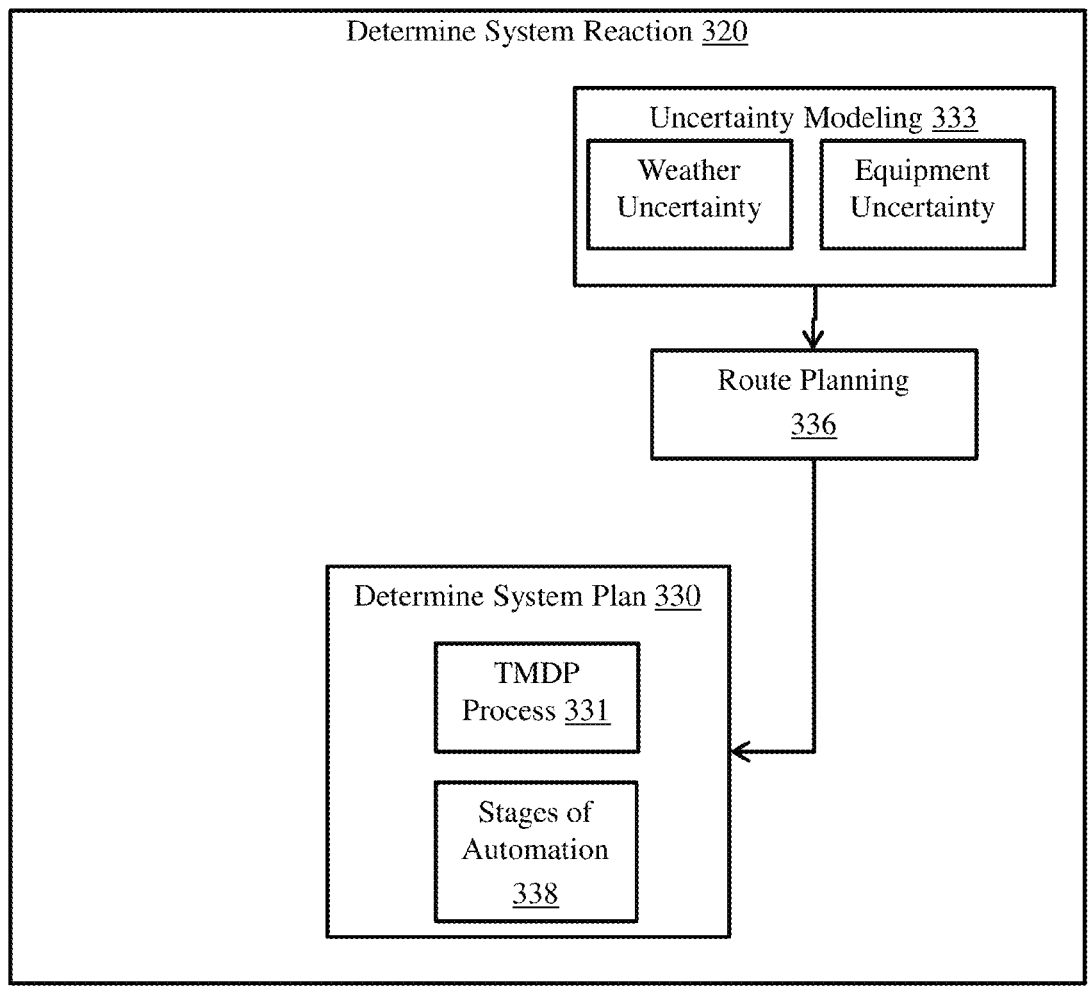
FIG. 3 is a process diagram of one example embodiment of a method of determining a system reaction.

A shown in FIG. 3, one embodiment of determining a system reaction at 320 comprises determining a system plan at 330 which may be performed by a decision-theoretic algorithm such as a TMDP process 331 as described in co-pending U.S. Pat. App. No. 61/612,043, filed on Mar. 16, 2012 which is incorporated by reference in its entirety. As shown, the determining of the system reaction may also include other methods such as uncertainty modeling methods at 333, route planning methods at 336 and stages of automation methods at 338. The determining a system reaction comprises determining what system plans may be feasible considering the environmental input. As shown, using input from results of the uncertainty modeling at 333, the route planning methods at 336 may generate a series of routes, or system plans, to react to the environmental input. These system plans, with characteristics for advantages and drawbacks, feed the methods to determine a system plan at 330 which analyses these system plans in light of information such as user state and hazard state. System plans are determined by optimizing plan selection and determining a series of characteristics for the system to implement the selected system reaction. An example of system characteristic may be the stage of automation at which the system will provide an automated response to the environmental uncertainty. For example, if a set of selected routes require immediate system reaction, the system may need a high level of automation so that the reaction is performed quickly without a need for direct user input.

Referring back to FIG. 1, with the system reaction determined, this reaction may be communicated to the user interface at 140. The user interface may utilize data from the planning methods to manage user alerts and characterize the user functional state. The system may increase the intrusiveness of any system reaction or alarm and may guide the focus of the user based on the severity and urgency of the estimated hazard. The user interface may incorporate multi-modal information presentation to convey urgency and support information processing.

Also shown in FIG. 1, in some embodiments, the user state may also be used as an input to determine the system plan at 130 and the system reaction at 120. The user state reflects the human conditions that may bear on the user's behavior and actions such as but not limited to the user's physiology or environmental variables that may contribute to the mental effort, task demands, and ongoing performance as they may affect the user's workload. Determining the user state at 124 predicts the state of the user related to the environmental inputs received. As hazards can be related to hazard states, relationships can be defined between environmental input and the estimated state of a user, such as with a predictive index, such that the user state can be determined by correlating the environmental input received to at least one user measures to a predicted at least one user state utilizing the predictive index. A context model may also be used to estimate the user state at 124.

Figure 2B:
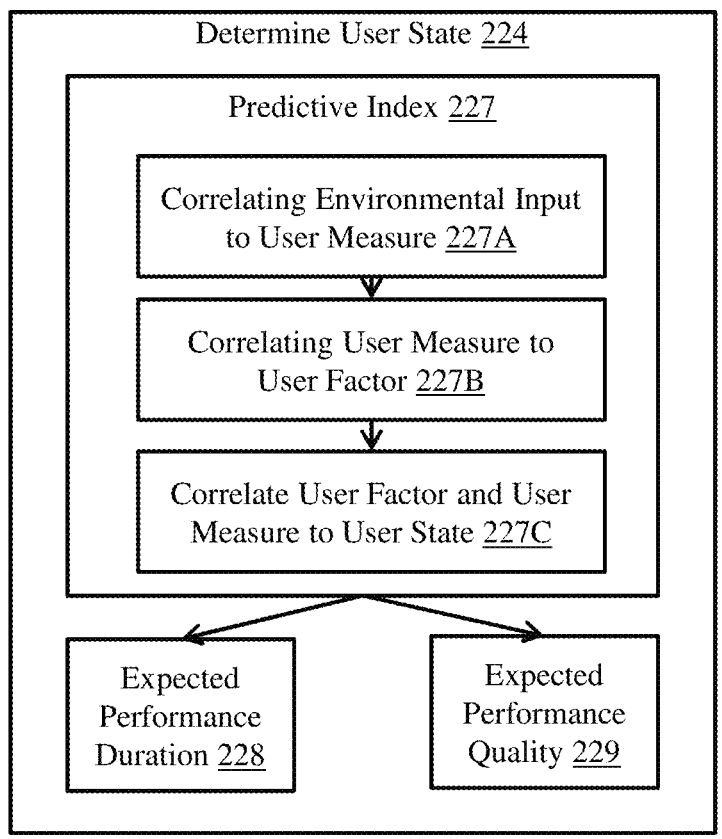
FIG. 2B is a process diagram of one example embodiment of a method of determining a user state.

In one embodiment, as shown in FIG. 2B, the user state may be determined at 224 by a predictive index 227 that correlates environmental inputs to user measures at 227A and correlates user measures to user factors such as mental effort, task demands and on-going task performance at 227B. From a correlation of these inputs and factors, a workload estimator algorithm may also be used to determine the user workload, or user state at 227C. These outputs may be further modulated by mediating variables, such as fatigue or situation awareness, which are defined through environmental and user sensing. The state may include an estimate of the expected performance quality the user may be able to provide at 229 and an expected performance duration at 228.

In some embodiments, automation may also be accounted for in the system reaction. In some embodiments, the methods also support complex decision making for process replanning and to deconflict planning with potential hazardous environmental inputs.

Some embodiments may be used to assist processes such as moving vehicles such as aircraft from Point A to Point B with greater efficiency. Some embodiments can utilize a user interface that can address (1) user information needs, (2) environmental uncertainty and risk, (3) potential advantages gained through multimodal information presentation, and (4) model-based, situationally aware display adaptation to support information processing and decision making.

Some embodiments of the methods and systems, with an aircraft pilot as a user, provide information acquisition support through CWA functions to capture the user's attention and notify the presence of the hazard, enhance information integration and inference through tools to support the user in assessing the hazard situation relative to ownship safety, and, when appropriate, provide decision support, recommending route planning changes to divert around or avoid safety-critical hazards.

One Example Embodiment of Methods to React to Environmental Input, ALARMS and Trajectory Based Operations Adaptive Information Display (TBO-AID):

One embodiment of methods of reacting to environmental input is described and shown for illustration purposes and not for limitation. Although this example embodiment is directed to a pilot, as a user, reacting to flying conditions, as one type of environmental input data, it is understood that the methods have broad applications such as for vehicle drivers reacting to surrounding environmental inputs.

Figure 4:
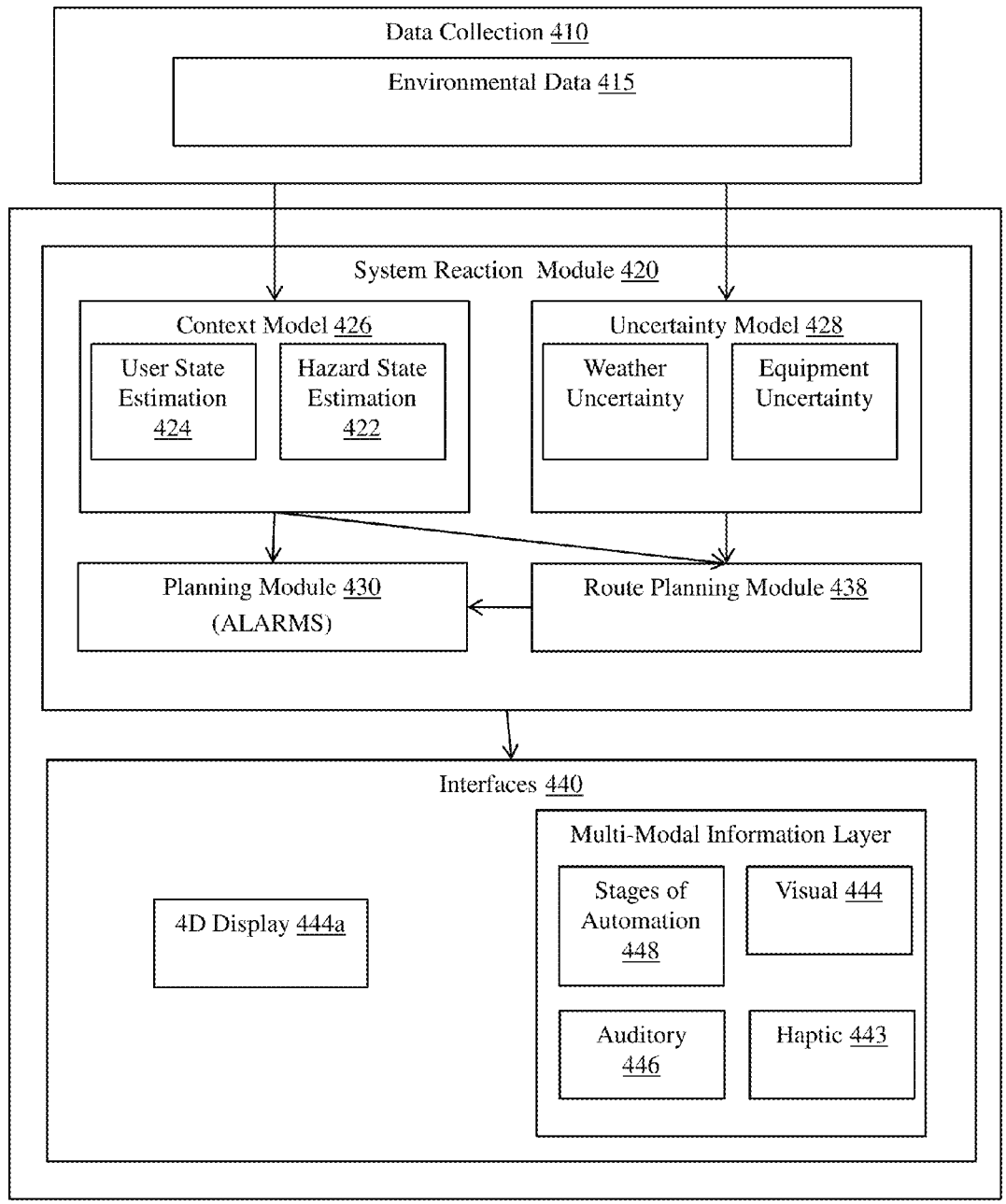
FIG. 4 is a functional diagram of one example embodiment of a system to react to environmental input including details of the planning model and the user interface.
Figure 5:
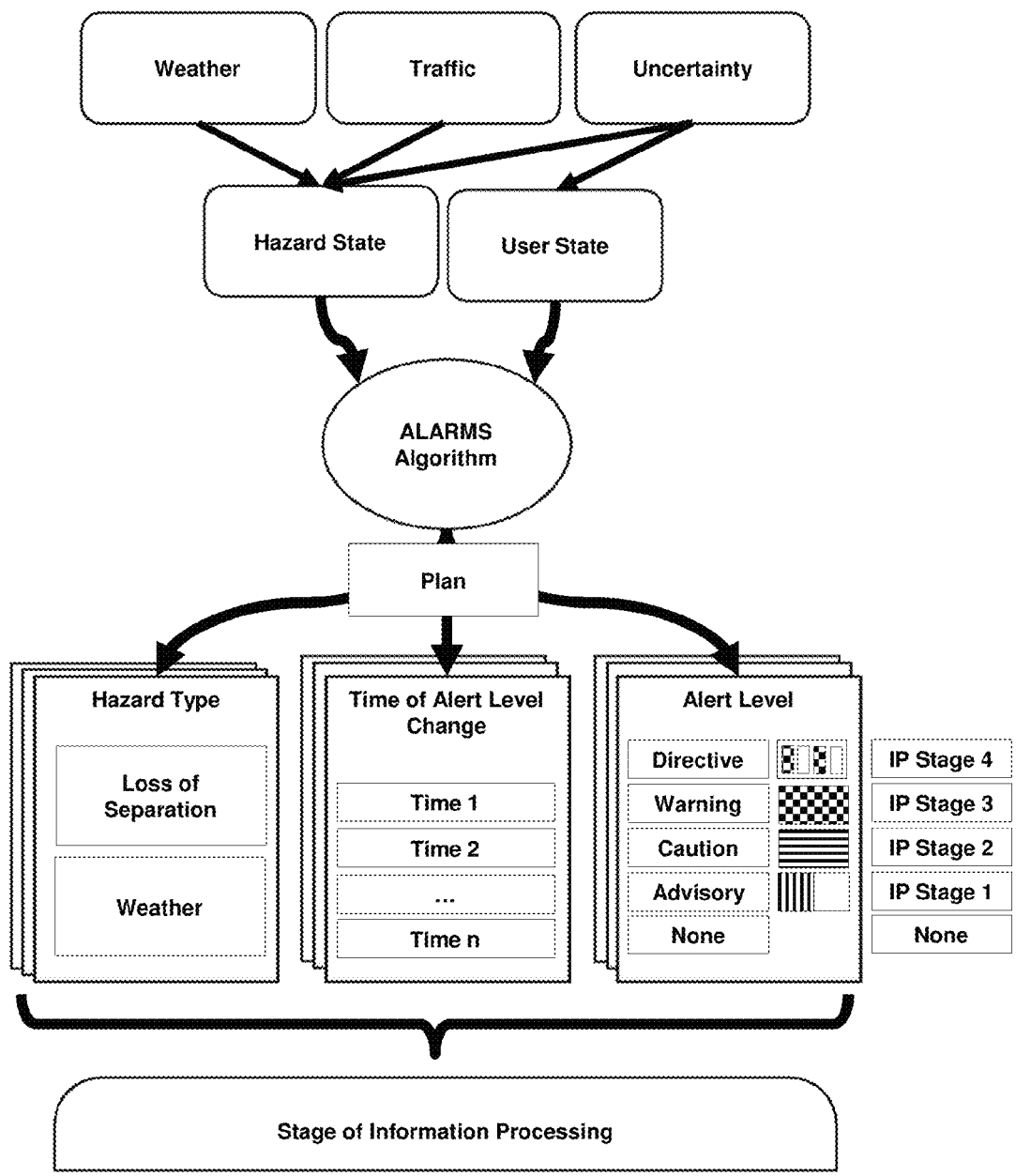
FIG. 5 is a functional diagram of one example embodiment of a system and method to react to environmental input.

One embodiment of the data collection and planning module, the ALerting And Reasoning Management System (ALARMS) approach, is detailed in FIGS. 4 and 5. These embodiments generally receive an environmental input, determine a hazard state and a user state from the environmental input, determine a system reaction from the hazard state and the user state and communicate the system reaction to a user interface.

In this embodiment, referring to FIG. 4, the Aircraft Simulation and Hardware-in-the-Loop Lab was used to identify the hazards and sensor systems, and quantify the relationship between them. The result of this analysis was used to construct probability tables for determining a hazard state with a hazard state estimation model, here a State Estimation Bayesian Network. One input to the State Estimation Bayesian Network is the alerts (e.g. weather and traffic) issued by the sensor systems on the aircraft. The output is an estimate of the probability and severity estimate of the underlying hazards.

As an illustration of the hazard state estimation model used in this embodiment is shown in FIGS. 6A and 6B where the hazard state is determined through the use of a Bayesian Network that exploits a hazard matrix 623. The hazard matrix 623, an example of which is at FIG. 6A, is a set of relationships linking potential hazards during operations and sensor signals provided to users for the purpose of alerting them to these hazards. The hazard matrix may be a table relating a type of hazard to an environmental input or sensor and a severity level of the hazard (i.e. A, W (Black) and C). These relationships may be gained through tools such as CWA. The data from the hazard matrix 623, populated with current and future technologies and/or sensors, forms the basis of the Bayesian Network 621, which takes in the alerts issued by the sensor systems. As shown in FIG. 6B, the Bayesian Network 621 weighs these inputs and associates them with the probability of hazards based on the inputs. Using a model of the system's environment, the Bayesian Network 621 outputs a probability distribution of the various hazards. The output of the hazard state estimation model may be an estimate of the probability and severity of the hazards indicated by the sensor input.

Figure 7:
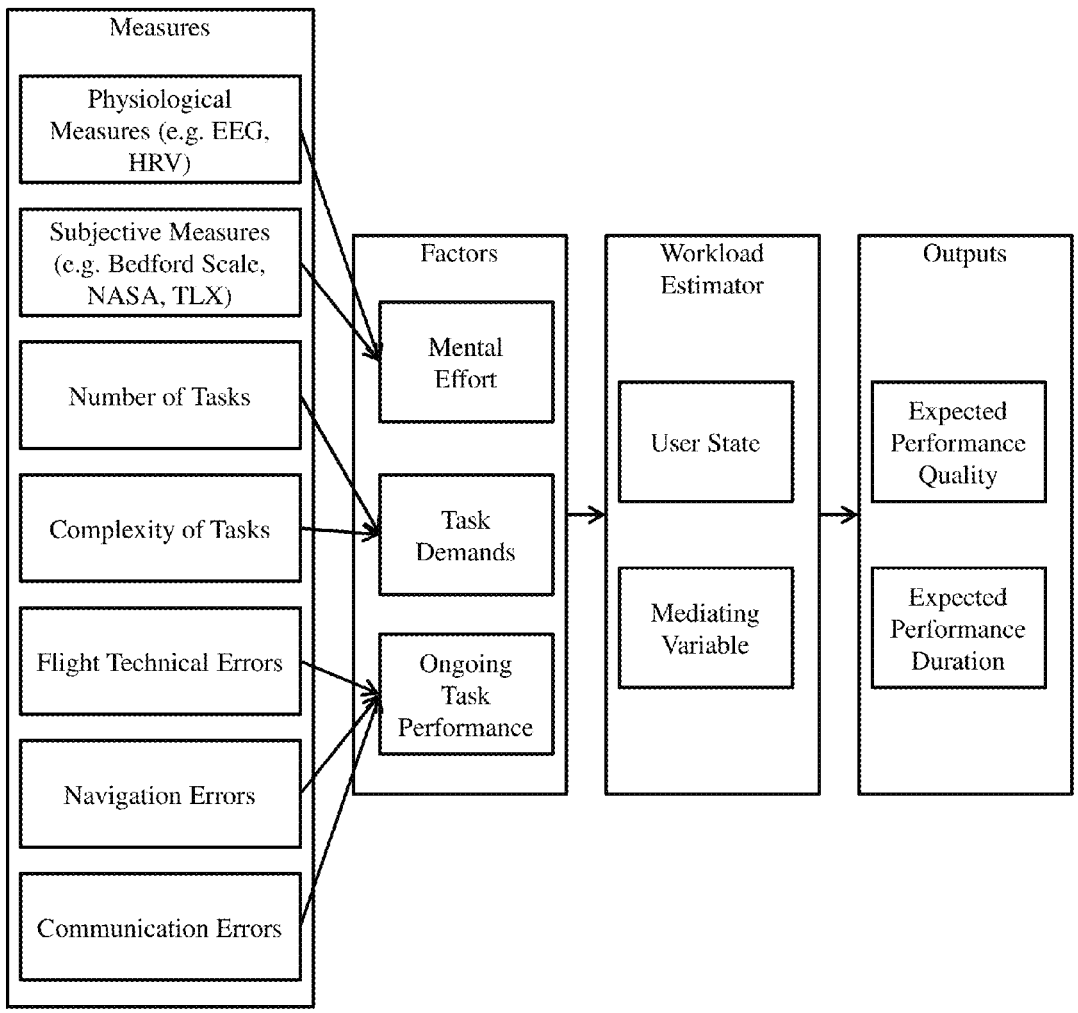
FIG. 7 is a functional diagram of an example method of determining a user state.

Referring to FIG. 7, a context model may also be used to estimate the user state. The user's state may be obtained by correlating the sensor environmental input into measures, in this instance user measures. The user measure may be any representation of whether the user measure is present. The user measure may be a binary measure or it may be a numeric or vector representation of a variability of the measure. For example, as shown, user measures may be representations of input such as physiological measures, subjective measures, number of task required, complexity of the tasks or errors in performing the tasks. The user measures are then put into an interpreter, such as a predictive index, to estimate the true state of the user given the user measures. In some embodiments, the user state may be determined by a predictive index that correlates environmental inputs or user measures to user factors such as mental effort, task demands and on-going task performance. The user factor may be any representation of whether the user factor is present or it may be a numeric representation, as a user factor measure, of a variability of the user factor. For example, if one user factor is more important than another, a first user factor may be weighted more that a second user factor in estimating the user state. User factors, as shown may comprise mental effort, task demands or ongoing task performance. From these user and factor measures, a workload estimator algorithm may also be used to determine the user workload, or user state. The workload estimator algorithm may be an algorithm such as a sum of the measures, weighted by the user factors. The workload estimator may define the user state in the form of two outputs: an estimate of the expected performance quality the user may provide and an estimate of the expected performance duration. These outputs may be further modulated by mediating variables, such as fatigue or situation awareness, which are defined through environmental and user sensing.

Referring back to FIG. 4, once the hazard and pilot state are estimated, the information is sent to the planning algorithm (ALARMS), which may determine the plan to address the hazards. Generally, a decision-theoretic algorithm, such as but not limited to a TDMP, may be used to produce the temporal plan. In this embodiment, the planning algorithm is a TMDP model. (Boyan and Littman, 2000). The TMDP model can be used to capture both state uncertainty in the environment as well as duration uncertainty in human (pilot) actions (Schurr and Marecki, 2008). Its input is the hazard and user states. In some embodiments, a Markov model of the effectiveness of the pilot and automation in handling the hazards, given various levels of alert may also be inputs to the planning algorithm. Its output is a representation of a system reaction, such as a plan for addressing the hazard. In some embodiments, the output is a time-dependent plan for addressing the hazard. In some embodiments, an uncertainty model may be used to capture both state uncertainty in the environment as well as duration uncertainty in human (user) actions. For example, the uncertainty model may analyze the amount of ambiguity associated with weather and traffic information being collected from the system, and then uses this information to feed the route planning module. The uncertainty information can be used to feed the visual component of the user interface by embedding visual elements to indicate the level of uncertainty associated with each visual element (e.g. location and speed of aircraft and weather). The system reaction may be further interpreted by the stages of automation module at the user interface which interprets the level of automation and decides a system reaction level, such as a level of alerts and options, to send to the user. This decision will then be sent to the user interface, which displays the information to the user.

In some embodiments, the system reaction may include a system reaction level. The system reaction levels reflect different system reactions as responses to the environmental input provided. The system reaction level may include a salience component and an intrusiveness component. The salience component defines how much information should be included in the system reaction. For example, the salience component may require more specific context-appropriate information to be provided to the user interface for a hazard detected by one sensor but will require less detailed information to the user interface for a sensor that does not detect a hazard. As another example, the salience component may define several map elements to be displayed on an interface when the hazard level is low but may require fewer map elements, the more context important elements, be displayed when the hazard state is higher. For illustration only, and not for limitation, examples of potential variables to be defined and required by the salience component may be visual weather information color-coded for different hazard levels, color-coded information reflecting hazards proximal to the user, multiple routing options based on the hazard level, varying audible warnings based on the hazard level and varying textual information based on the hazard level. The intrusiveness component defines how intrusive the system reaction should be. For example, the intrusiveness component may require a more intrusive alert, such as a haptic alert, when a hazard is imminent. For illustration only, and not for limitation, examples of potential variables to be defined by the intrusiveness component may be increasing levels of audible warnings as the hazard state increase, more intrusive visual warnings as the hazard level increases, increased haptic warnings, such as shaking of a steering wheel, as the hazard level increases, different coloring of hazards on a graphic interface as the hazard level increases or an increased combination of these variables as the hazard level increases. The system reaction level, to include the salience and intrusiveness components, may be defined according to the different stages of automation as described below. Further examples of system reaction levels, and suitable variables for the salience and intrusiveness components, are described in co-pending U.S. Pat. App. No. 61/558,487, filed on Nov. 11, 2012, the entire contents of which are incorporated herein by reference.

The stages of automation (Parasuraman et al., 2000) represent different information presentation techniques reflecting the capabilities of a user or system to utilize or react to that information. Examples of the stages for information presentation can include:

(Stage 1) Information Acquisition: Aiding to support the perception of, and attention to, relevant information in the environment. Within a TBO context, information acquisition automation can support the allocation of pilot attention to critical entities (e.g., weather cells, non-equipped aircraft) within the surrounding airspace.

(Stage 2) Information Analysis: Display concepts to assist in the integration and understanding of information. Within a TBO context, information analysis automation can be used to convey the present and predicted future locations of aircrafts relative to ownship's trajectory.

(Stage 3) Decision Selection: Decision support for identifying feasible actions and/or making optimal decisions. Within a TBO context, decision selection automation can provide recommendations for trajectory changes to accommodate weather developments.

(Stage 4) Action Execution: Means of implementing the action(s) selected. Within a TBO context, action execution automation can send commands to the aircraft control and communications system to implement the decisions.

As shown in FIGS. 8A-8C, the stage of automation may be used to correlate the system reaction level to context-appropriate information for user interfaces utilizing visual, auditory, and/or haptic means. Multimodal display designs can be used to present information and alarms according to the automation stage model, leveraging empirical research for determining effective applications of each modality. FIG. 8B shows a mapping of the user state to a hazard state. FIG. 8C shows a mapping of the system reaction level (e.g., adjustable attention, audio/tactile outputs) to hazard states and to information processing stages.

In some embodiments, the system reaction level is determined for different points in time. In conjunction with the recommended level of alert that may be supplied by the system reaction, the multimodal interfaces may provide context-appropriate information. This framework allows the user interface to support situation awareness and high quality decision making. In some embodiments, the system reaction may incorporate an appropriate level of automation which best addresses hazards in a time-dependent environment.

Discussed in detail later, the user interface receives the system reaction and communicates that system reaction to the user through means such as a graphic interface, haptic interface, multi-modal user interface or any other interface capable of communicating an alarm to a user. As used herein, the term haptic alert refers to any warning presented through the proprioceptive or kinesthetic senses, such as but not limited to a brake pulse deceleration/vehicle jerk, steering yoke vibration or pushback, joy stick vibration or pushback or seat vibration.

More details of one embodiment of the ALARMS approach, to include information on the algorithms used in the methods, are included and described in co-pending U.S. Pat. App. No. 61/612,043, filed on Mar. 16, 2012 entitled "SYSTEMS AND METHODS TO REACT TO ENVIRONMENTAL INPUT", the entire contents of which are incorporated herein by reference.

Figure 9:
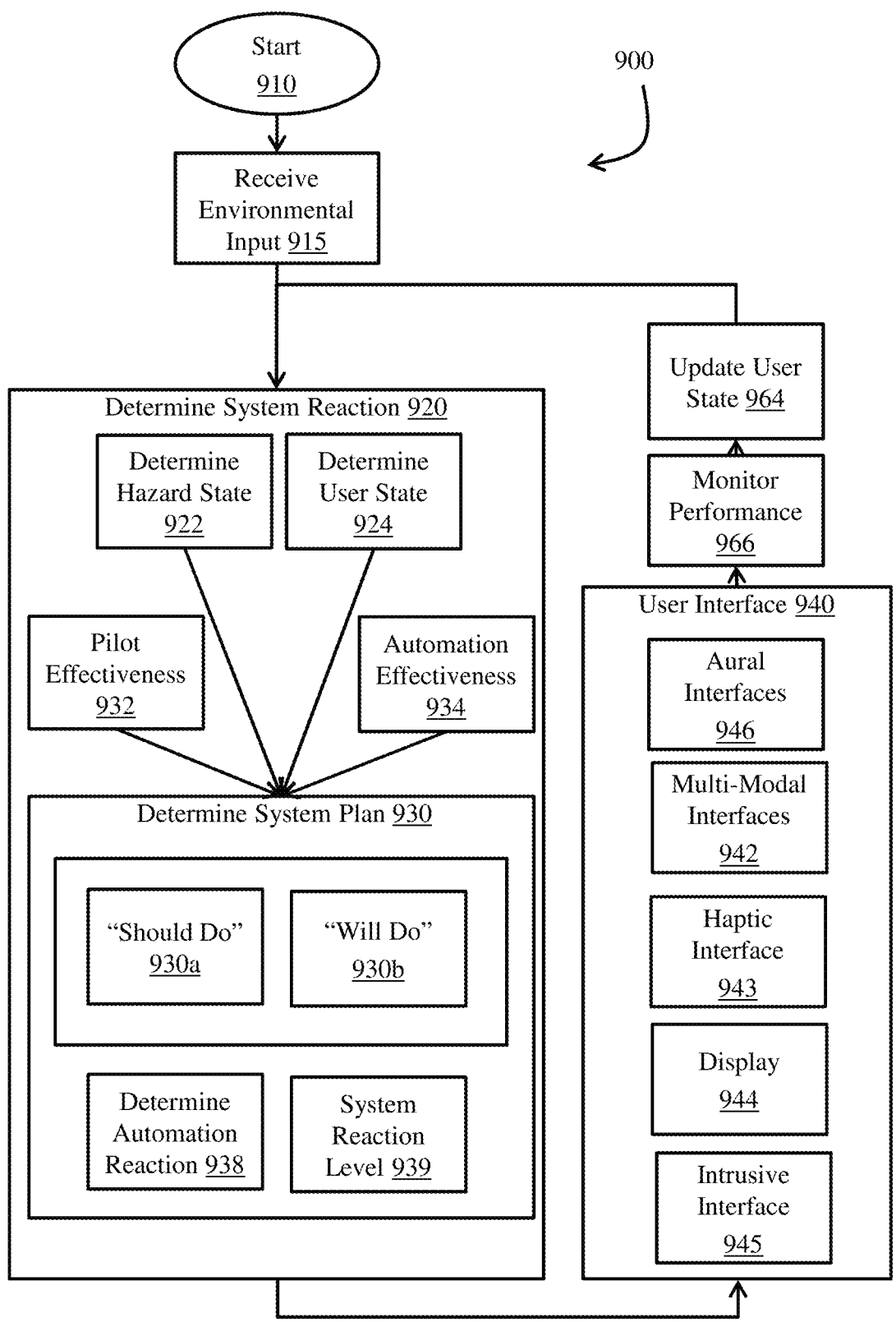
FIG. 9 is a process diagram of another example embodiment of a method to react to environmental input including example details of the planning model and the user interface.

FIG. 9 illustrates another embodiment of the method of determining a system reaction to environmental input. This embodiment 900 builds off of the concepts described in FIGS. 1, 4 and 5 and further includes methods to determine an automation system reaction at 938. The steps within determining a system reaction at 920 further include steps and modules to determine the automation effectiveness 934 and the pilot effectiveness 932. The planning module to determine system plan at 930 further includes steps to determine two different types of system reactions, "should do" system reactions at step 930a and "will do" system reactions at step 930b.

The automation reaction component, used to determine an automation reaction at 938, is the result of an interpretation of the system reaction output by the system. Based on the alert type and level specified in the plan, a rules-and-constraint-based algorithm determines the stage of automation for the automation reaction, and determines the content of the automation reaction in the form of a set of multi-modal automation responses, selected from a library of responses.

When an automation effectiveness component 934 and/or a user effectiveness component 932 are available, their outputs are used along with the hazard state and the user state to determine the automation reaction at 938. An optimization rules-and-constraint-based algorithm is employed to prune the automation reaction domain space and to build an automation reaction that maximizes system effectiveness based the current and future state estimates. In other words, not only is the automation reaction built to address the hazard and user state, but it is designed to be optimal considering the automation and user effectiveness knowledge.

FIG. 9 also includes more detail of the user interface 940. As implemented in the Trajectory Based Operations Adaptive Information Display (TBO AID) embodiment, the user interface may include interfaces such as a multi-modal user interfaces 942, a haptic interface 943, an intrusive interface 945, a display 944, an aural interface 946 or any combination of these interface types. This embodiment also monitors the performance of the user at 966 and using information from this monitoring to update to the user state at 964. The system uses this monitoring and input from the planning the system reaction methods to provide the system reaction and the system reaction level. Reflecting the severity and urgency of the impending hazard, the system reaction level may provide the intrusiveness component to reflect the intrusiveness of the alert and provide the salience component to guide the focus of the information support to the user. The user interface may incorporate a 4D display and incorporate the use of multimodal information presentation to convey urgency and support information processing. This interface is meant to supplement technologies by providing an additional means to access and explore information.

In this embodiment, the TBO-AID user interface 940 is driven by the planning module 920 to manage alerts and characterize operator functional state. TBO-AID uses this model to increase the intrusiveness of the alarm, through an intrusive user interface, as the system reaction level increases and guides the focus of the information support based on the severity and urgency of the impending hazard. The display may incorporate a 4D display 944 that allows pilots to investigate the current state of the surrounding airspace and promotes exploration of this space over time to support 4D TBO. In addition to a visual display, TBO-AID recognizes the salience component of the system reaction level and incorporates the use of multimodal information presentation (i.e., auditory and tactile modalities) to convey salience components such as urgency to support information processing. TBO-AID may supplement integrated NextGen flight deck technologies by providing an additional means to access and explore information. One possible method to integrate TBO-AID into the flight deck is to mount a tablet device directly on the steering yoke in glass cockpits to allow access for route planning and navigation.

TBO-AID can address moving aircraft from Point A to Point B with greater efficiency, saving time, money, and fuel. This flight deck technology supports 4D TBO by successfully implementing a user interface that specifically address: (1) unique information needs associated with conducting 4D operations (e.g., self-separation and route planning for deconfliction); (2) uncertainty and risk associated with weather and mixed-equipage conditions, key challenges for conducting 4D TBO; (3) advantages gained through multimodal information presentation; and (4) model-based, situationally aware display adaptation to support information processing and decision making.

The TBO-AID effort provides adaptable display concepts to support the unique information needs associated with 4D TBO.

Embodiments of the TBO-AID solution provide the following:

(1) Model-based techniques to convey information across multiple modalities to support 4D TBO. The visual component of the 4D display incorporated a multi-touch interface to promote naturalistic interaction, uncertainty and risk visualizations to enable more robust planning, and compatibility with concurrent display research being developed. Additionally, multiple sensory modalities may supplement the visual component to convey information and cue the pilot to impending hazards.

(2) Use of existing, proven framework for stages of automation to guide information presentation. TBO-AID supports pilot information processing via the stages of automation (Parasuraman et al., 2000) paradigm. Different interface concepts are possible to support information acquisition, information analysis, or decision selection depending on the context of the ongoing situation. Utilizing situationally-aware context models to process relevant data and drive displays may provide a robust approach for effectively adapting displays based on dynamically changing needs. The Federal Aviation Administration Human Factors Design Standard and known principles for display design may be used for defining the user interface. It is possible to use this framework to modulate the number, nature, and intensity of alerts by appropriately scaling the intrusiveness and attention of signals across the visual, auditory, and tactile channels to optimally manage impending hazards. This "adjustable attention" may provide the pilot with the right prompting at the right time.

Another embodiment of the methods to react to environmental input comprises integrating the methods to define the user state as described above, into other systems that react to environment input. As one example embodiment, the collision avoidance systems defined in U.S. Pat. No. 7,245,231 ("Kiefer"), issued on Jul. 17, 2007 to Raymond J. Kiefer at al., the entire contents of which are incorporated by reference in their entirety, could be enhanced with the user state to provide a more robust system reaction. The Keifer system could be enhanced with a sensor to detect environmental input such as body movement, eye movement or hand pressure to be used as user measures. The user measures, factored or not, could be used to define the user state and together with environmental data from the defined sensor as hazard measures a system reaction could be provided that takes into account both the hazard and the user state. Embodiments could be further enhanced with the user interfaces described herein, the temporal planning described herein and the system reaction levels described.

Embodiments of the methods to react to environmental input could also enhance solutions like Kiefer by incorporating the planning elements described herein into that solution. For example, in addition to alerting on the presence of a hazard, the planning methods described above could be incorporated such that a temporal plan is determined as a system reaction and at one point in the sequence of activities against the plan, one alarm may be given at the system reaction and at another point in the sequence of activities against the plan, another alarm may be given as the system reaction. Systems such as Kiefer may also be enhanced to accommodate the uncertainty and automation as described above.

Embodiments of the methods to react to environmental input could also enhance solutions like Kiefer by incorporating the system reaction levels described herein into that solution. For example, in addition to alerting on the presence of a hazard, the system reaction could include system reaction level information such as the salience and/or the intrusiveness component to user interfaces as described herein.

One Embodiment of the Systems to React to Environmental Input:

One embodiment of the environmental system reaction system generally comprises the functional elements of FIG. 1 4, 5 or 9 in a software program product to be executed by a computer implemented system.

As will be readily apparent to those skilled in the art, the environmental system reaction systems and methods can be embodied in hardware, software, or a combination of hardware and software. For example, a computer system or server system, or other computer implemented apparatus combining hardware and software adapted for carrying out the methods described herein, may be suitable. One embodiment of a combination of hardware and software could be a general purpose computer system with a computer program that, when loaded and executed, carries out the respective methods described herein. In some embodiments, a specific use computer, containing specialized hardware for carrying out one or more of the instructions of the computer program, may be utilized. In some embodiments, the computer system may comprise a device such as, but not limited to a digital phone, cellular phone, laptop computer, desktop computer, digital assistant, server or server/client system.

Computer program, software program, program, software or program code in the present context mean any expression, in any language, code or notation, of a set of instructions readable by a processor or computer system, intended to cause a system having an information processing capability to perform a particular function or bring about a certain result either directly or after either or both of the following: (a) conversion to another language, code or notation; and (b) reproduction in a different material form. A computer program can be written in any form of programming language, including compiled or interpreted languages, and it can be deployed in any form, including as a stand-alone program or as a module, component, subroutine, or other unit suitable for use in a computing environment.

Figure 10:
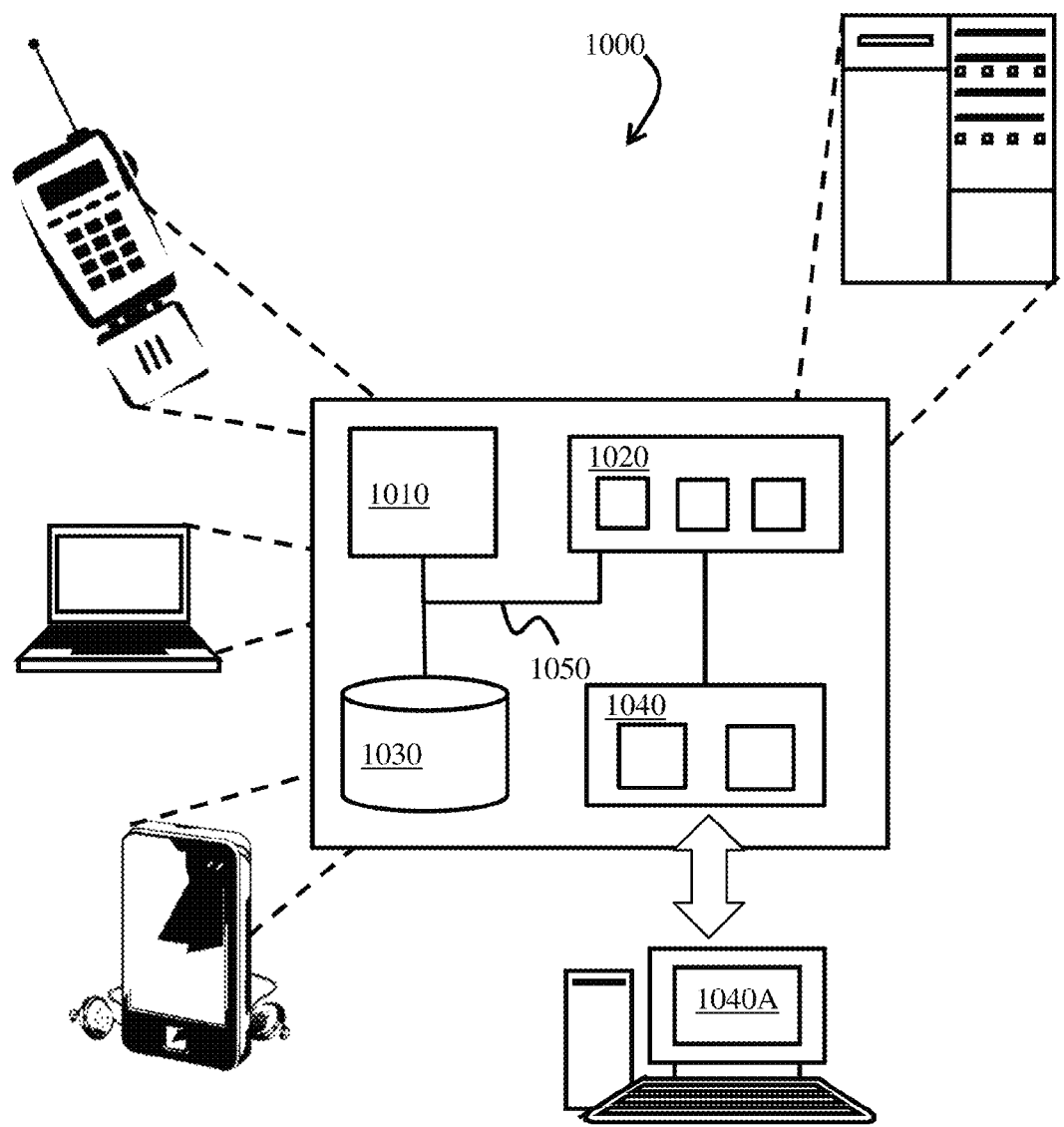
FIG. 10 illustrates one example embodiment of a computer system suitable for an environmental system reaction system.

FIG. 10 is a schematic diagram of one embodiment of a computer system 1000 by which the environmental system reaction methods may be carried out. The computer system 1000 can be used for the operations described in association with any of the computer implemented methods described herein. The computer system 1000 includes at least one processor 1010, a memory 1020 and an input/output device 1040. Each of the components 1010, 1020, and 1040 are operably coupled or interconnected using a system bus 1050. The computer system 1000 may further comprise a storage device 1030 operably coupled or interconnected with the system bus 1050.

The processor 1010 is capable of receiving the instructions and/or data and processing the instructions of a computer program for execution within the computer system 1000. In some embodiments, the processor 1010 is a single-threaded processor. In some embodiments, the processor 1010 is a multi-threaded processor. The processor 1010 is capable of processing instructions of a computer stored in the memory 1020 or on the storage device 1030 to communicate information to the input/output device 1040. Suitable processors for the execution of the computer program instruction include, by way of example, both general and special purpose microprocessors, and a sole processor or one of multiple processors of any kind of computer.

The memory 1020 stores information within the computer system 1000. Memory 1020 may comprise a magnetic disk such as an internal hard disk or removable disk; a magneto-optical disk; an optical disk; or a semiconductor memory device such as PROM, EPROM, EEPROM or a flash memory device. In some embodiments, the memory 1020 comprises a transitory or non-transitory computer readable medium. In some embodiments, the memory 1020 is a volatile memory unit. In some embodiments, the memory 1020 is a non-volatile memory unit.

The processor 1010 and the memory 1020 can be supplemented by, or incorporated in, ASICs (application-specific integrated circuits).

The storage device 1030 may be capable of providing mass storage for the system 1000. In various embodiments, the storage device 1030 may be, for example only and not for limitation, a computer readable medium such as a floppy disk, a hard disk, an optical disk, a tape device, CD-ROM and DVD-ROM disks, alone or with a device to read the computer readable medium, or any other means known to the skilled artisan for providing the computer program to the computer system for execution thereby. In some embodiments, the storage device 1030 comprises a transitory or non-transitory computer readable medium.

In some embodiments, the memory 1020 and/or the storage device 1030 may be located on a remote system such as a server system, coupled to the processor 1010 via a network interface, such as an Ethernet interface.

The input/output device 1040 provides input/output operations for the system 1000 and may be in communication with a user interface 1040A as shown. In one embodiment, the input/output device 1040 includes a keyboard and/or pointing device. In some embodiments, the input/output device 1040 includes a display unit for displaying graphical user interfaces or the input/output device 1040 may comprise a touchscreen. In some embodiments, the user interface 1040A comprises devices such as, but not limited to a keyboard, pointing device, display device or a touchscreen that provides a user with an ability for communicating with the input/output device 1040.

The computer system 1000 can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system may be connected by any form or medium of digital data communication such as a communication network. Examples of communication networks include, e.g., a LAN, a WAN, wireless phone networks and the computers and networks forming the Internet.

Figure 11:
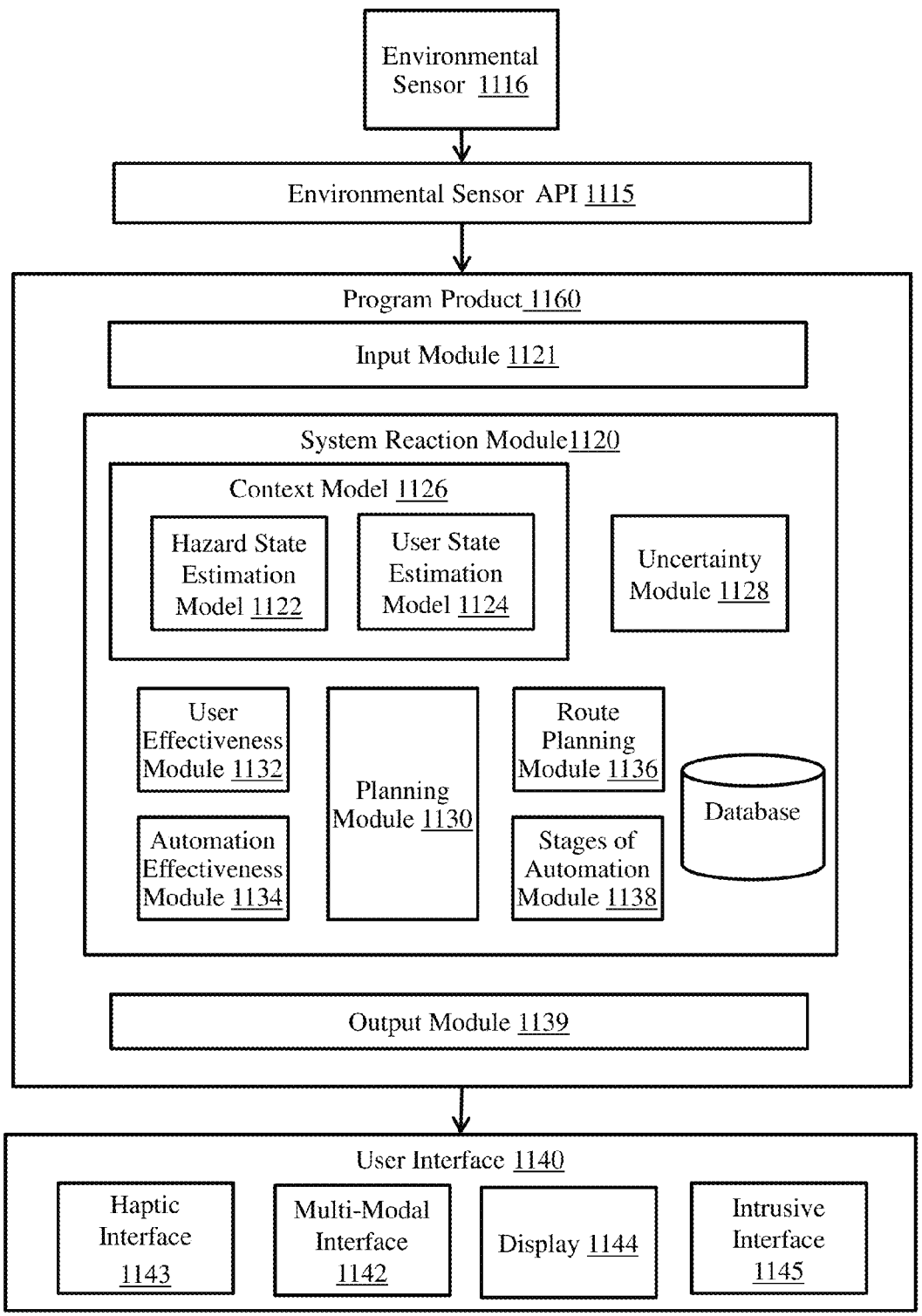
FIG. 11 illustrates a functional diagram of one embodiment of a program product suitable for an environmental system reaction system.

A functional diagram of one embodiment of the computer program product implemented on a generic computer system capable of executing the described methods is shown in the functional diagram in FIG. 11. An environmental sensor 1116 collects environmental data and transmits it to a generic computer system having a computer program product 1160 via an environmental sensor application program interface (API) 1115. In the computer program product 1160, an input module 1121 receives the environmental data and formats it in a manner understandable by a computer program. The environmental data, in its new format, is communicated to the system reaction module 1120 and its context model 1126, which comprises a model for hazard state estimation 1122 and a model for user state estimation 1124. The output of the user and hazard state models (information about hazard and user states) is communicated to the planning module 1130, which may also receive input from a user effectiveness module 1132 and an automation effectiveness module 1134. The user effectiveness and automation effectiveness modules define, respectively, effectiveness measures for the user and the automated system the user is employing. These measures inform the planning module 1130 as to the quality of possible plans that may be generated. These plans, or a selected one of the plans may be communicated to the output module 1139 as the system reaction. Optionally, as input to the plans or using the plans generated, a route planning module 1136 may also be used to define operational characteristics and parameters for the possible flight plans, and a stages of automation module 1138 defines the appropriate levels of automation for the flight systems according to these plans. An uncertainty module 1128 may be used to model the uncertainty affecting all data being employed by the various models and modules enabling the optimization of data use. A database is integrated into the planning component to store and allow for data exchange. When the route planning module 1136 and the stages of automation module 1138 are used, their products are communicated to the planning module 1130 or the output module 1139 which formats the planning components to output them to external systems. The user interface 1140 receives these components and may communicate the related information in fashions such as: through a multi-modal interface 1142 which connects to other parts of the aircraft, or through a visual display 1144, a haptic interface 1143 or an intrusive interface 1145 available to the pilots. An aural user interface may also be used.

One example embodiment of the environmental system reaction systems and methods may be embodied in a computer program product, the computer program product comprising a computer readable medium having a computer readable program code tangibly embodied therewith, the computer program code configured to implement the methods described herein, and which, when loaded in a computer system comprising a processor, is able to carry out these methods.

Another embodiment of an environmental system reaction system is shown in FIG. 4 and generally comprises the data collection module 410 to collect the environmental data 415 shown, the system reaction module 420, and the interface module identified as the interfaces 440. In this embodiment, the environmental system reaction system is an integrated flight deck tool that facilitates NextGen technology by supporting more complex, strategic decision making for navigation in TBO and route replanning to deconflict with potential environmental and traffic hazards. The data collection module 410 continually collects sensor data (environmental data or simulated sensor data), that exist in the environment, such as information about aircraft status, local traffic, weather, and the pilot's physiology and other state variables. The sensors on the Flight Deck (current and NextGen) perceive these hazards. This data is continually being collected in real time using a data collection tool that receives this raw environmental sensor data and converts it to a format to be used by the system reaction module 420. The system reaction module 420 comprises a context model 426 and an uncertainty model 428 that considers the reliability of information. The context model is able to translate the environmental input data into appropriate measures to estimate user and hazard states. The context model includes a component that analyzes the hazard state 422, or the condition of potential safety threats (i.e., the severity, type, and time-to-act of potential traffic and weather conflicts). The hazard state estimation model 422 uses information about aircraft sensor alerts and Bayesian reasoning to deduce the set of true existing hazards. Bayesian reasoning is a type of probabilistic reasoning particularly well suited to define the hazard state because it can account for uncertainty in sensor data and environment modeling. The context model also estimates the pilot (user) state 424 by analyzing measures that contribute to mental effort, task demands, and ongoing performance as a gauge for pilot workload. The hazard information is combined with the pilot workload to generate a temporal plan as a system reaction (via the planning module 430). As shown, this plan may include routing information to address the hazards (via the route planning module 438). As part of this plan, a stage of automation (Parasuraman et al., 2000) may be recommended for each hazard at each point in time of the temporal plan. In this embodiment, the uncertainty model 428 considers the amount of ambiguity associated with environmental data such as weather and traffic information being collected from the system, and uses this information to feed the route planning module 438. The uncertainty information is also used to feed the user interface 440, such as a visual component 444 of the adaptive multimodal interface 440 by embedding visual elements to indicate the level of uncertainty associated with each visual element (i.e., location and speed of aircraft and weather). In this embodiment, the plan is further interpreted by a stages of automation module 448, which can interpret the stage of automation provided in the system reaction and decide what system reaction level, or which level of a plurality of levels of alerts and options, to send to the pilot. This determination, as a system reaction, will then be sent to the user interface 440, which presents the information to the user through visual displays or other means.

In conjunction with the recommended system reaction supplied by the system reaction module 420, the multimodal interfaces provide context-appropriate information for user interfaces utilizing visual 444, auditory 446, haptic 443 and/or 4D display 444a means. This framework adapts the user interface to support situation awareness and high quality decision making. Multimodal display designs can be used to present information and alarms according to the automation stage model, leveraging empirical research for determining effective applications of each modality.

Although this invention has been described in the above forms with a certain degree of particularity, it is understood that the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention which is defined in the claims and their equivalents.

We claim:

1. A computer implemented method of determining a system reaction to an environmental input, said method comprising:
   receiving a first environmental input and a second environmental input;
   the first environmental input provided by a sensor system on a vehicle;
   determining a hazard state from the first environmental input;
   determining a user state from the second environmental input;
   the user state comprising a user workload;
   determining an automation reaction from an automation effectiveness component and a user effectiveness component;
   the automation reaction comprising at least one of a set of automation responses;
   determining a system reaction from the hazard state, the user state and the automation reaction; and
   communicating the system reaction to a user interface.

2. The computer implemented method of claim 1 wherein determining the user state from the second environmental input comprises determining the user state from the second environmental input in the form of an estimate of an expected user performance quality and an estimate of an expected user performance duration.

3. The computer implemented method of claim 1 wherein the user workload comprises at least one selected from a group comprising a task demand and an on-going task performance.

4. The computer implemented method of claim 1 wherein determining the system reaction from the hazard state and the user state comprises determining a system reaction from the hazard state, the user state and an uncertainty model.

5. The computer implemented method of claim 1 wherein:
   the set of automation responses comprises a set of routes for the vehicle;
   the second environmental input provided by a sensor configured to sense a physiological measure of a driver of the vehicle; and
   the system reaction comprises sending a command to a control and communications system of the vehicle to implement the set of routes without a direct input from the driver.

6. The computer implemented method of claim 5 wherein the vehicle is an aircraft.

7. The computer implemented method of claim 1 wherein determining the system reaction from the hazard state, the user state and the automation reaction comprises determining the system reaction from the hazard state, the user state, the automation reaction and an uncertainty model.

8. The computer implemented method of claim 7 wherein:
the system reaction comprises a temporal plan;
the temporal plan comprises a multi-step plan comprising a series of routes;
determining the user state from the second environmental input comprises determining the user state from the second environmental input in the form of an estimate of an expected user performance quality and an estimate of an expected user performance duration; and
the system reaction comprises a salience component and an intrusiveness component.

9. The computer implemented method of claim 1 wherein the automation effectiveness component comprises an effectiveness measure of an automated system to handle the hazard state and the user effectiveness component comprises an effectiveness measure of a user to handle the hazard state.

10. A computer implemented method of communicating a system reaction to an environmental input, said method comprising:
receiving an environmental input from a sensor on a vehicle;
determining a hazard state from the environmental input;
determining a system reaction from the hazard state;
the system reaction comprising an optimum plan from a plurality of temporal plans;
each temporal plan comprises a multi-step plan comprising a series of routes; and
communicating the system reaction to a user interface.

11. The computer implemented method of claim 10 wherein determining the system reaction from the hazard state comprises determining the system reaction from the hazard state and a user state.

12. The computer implemented method of claim 11 wherein the user state is determined from the environmental input in the form of an estimate of an expected user performance quality and an estimate of an expected user performance duration.

13. The computer implemented method of claim 11 wherein:
the user state is determined by correlating the environmental input to the user state utilizing a predictive index; and
the hazard state is determined by estimating the hazard state with a State Estimation Bayesian Network.

14. The computer implemented method of claim 10 wherein determining the system reaction from the hazard state comprises determining the system reaction from the hazard state, a user state, an uncertainty model and an automation reaction.

15. The computer implemented method of claim 10 wherein determining the system reaction comprises determining a multi-step plan from a Time-Dependent Markov Decision Process.

16. The computer implemented method of claim 10 wherein:
the vehicle comprises an aircraft;
the multi-step plan comprises a set of routes for the aircraft;
determining a user state from a second environmental input;
the second environmental input provided by a sensor configure to sense a physiological measure of a pilot of the aircraft;
the system reaction further comprises sending a command to a control and communications system of the aircraft to implement the set of routes without a direct input from the pilot.

17. The computer implemented method of claim 10 wherein the system reaction comprises sending a command to a control and communications system of the vehicle to implement the series of routes without a direct input from a user.

18. The computer implemented method of claim 10 wherein:
the user interface is a multi-modal user interface having a level of alert;
the system reaction further comprises a system reaction level; and
the level of alert corresponds to the system reaction level.

19. The computer implemented method of claim 10 wherein determining the system reaction from the hazard state comprises determining the system reaction from the hazard state and an uncertainty model.

20. A computer program product for determining a system reaction to an environmental input comprising a non-transitory computer readable medium having a computer readable program code embodied therein, said computer readable program code configured to be executed to implement a method for determining a system reaction to an environmental input, said method comprising:
receiving an environmental input from a sensor on a vehicle;
determining a hazard state from the environmental input;
determining a temporal plan from the hazard state;
determine a system reaction from an optimum plan from a plurality of the temporal plan;
each temporal plan comprises a multi-step plan comprising a series of routes; and
communicating the system reaction to a user interface.

* * * * *